US008689704B2

(12) United States Patent
Hodges et al.

(10) Patent No.: US 8,689,704 B2
(45) Date of Patent: Apr. 8, 2014

(54) ADJUSTABLE BI-LEVEL SURGICAL ACCESSORY TABLE

(76) Inventors: Scott D. Hodges, Oultewah, TN (US); S. Craig Humphreys, Chattanooga, TN (US); Ira B. Young, Chattanooga, TN (US); Christopher B. Young, Chattanooga, TN (US)

( * ) Notice: Subject to any disclaimer, the term of this patent is extended or adjusted under 35 U.S.C. 154(b) by 0 days.

(21) Appl. No.: 13/155,223

(22) Filed: Jun. 7, 2011

(65) Prior Publication Data

US 2012/0137935 A1 Jun. 7, 2012

Related U.S. Application Data

(63) Continuation-in-part of application No. 11/948,089, filed on Nov. 30, 2007, now abandoned, which is a continuation-in-part of application No. 11/436,609, filed on May 19, 2006, now abandoned.

(60) Provisional application No. 60/682,851, filed on May 20, 2005.

(51) Int. Cl.
*A47F 5/12* (2006.01)
*A47B 95/02* (2006.01)

(52) U.S. Cl.
USPC ............ 108/5; 312/319.9; 108/102; 108/143

(58) Field of Classification Search
USPC ................ 108/1–10, 42, 49, 59, 180, 182, 108/186–193, 137, 143, 153.1, 157.1, 108/157.18–158.12, 92–105; 312/319.9
See application file for complete search history.

(56) References Cited

U.S. PATENT DOCUMENTS

| | | | |
|---|---|---|---|
| 1,422,101 A | 7/1922 | Holmes | |
| 1,867,763 A | 7/1932 | Rose | |
| 1,969,749 A | 8/1934 | Harsh | |
| 2,124,349 A * | 7/1938 | Herbster | 49/263 |
| 2,348,955 A * | 5/1944 | Buchanan | 292/255 |
| 2,730,423 A | 1/1956 | Mock | |
| 2,747,343 A | 5/1956 | Gellert | |
| 2,791,003 A | 5/1957 | Berger | |
| 3,358,620 A * | 12/1967 | Parigi | 108/6 |
| 3,364,621 A * | 1/1968 | Erickson | 49/263 |
| 3,364,881 A * | 1/1968 | Kooi | 108/10 |
| 3,557,791 A | 1/1971 | Duffy | |
| 3,597,033 A | 8/1971 | Slouka | |
| 3,715,972 A | 2/1973 | Kelso et al. | |
| 3,768,971 A | 10/1973 | Fishpaw | |

(Continued)

FOREIGN PATENT DOCUMENTS

| | | |
|---|---|---|
| DE | 10200916 | 7/2003 |
| DE | 10329542 | 2/2004 |

*Primary Examiner* — Darnell Jayne
*Assistant Examiner* — Timothy M Ayres
(74) *Attorney, Agent, or Firm* — Shoemaker and Mattare (57) ABSTRACT

A sterilizable surgical accessory table includes a pair of independently movable tabletops supported by a base. The front tabletop is supported by a carriage which allows the position of the front tabletop to be adjusted fore and aft, while maintaining it in a horizontal plane. The rear tabletop cannot move fore and aft, but it can be tilted about a transverse horizontal axis. The rear tabletop is at all times well above the horizontal plane of the front tabletop. Both tabletops are normally locked in position, but the setting of each can be adjusted by depressing one of two pedals at the bottom of the base. The tabletops can be removed easily for cleaning and sterilization.

17 Claims, 7 Drawing Sheets

(56) References Cited

U.S. PATENT DOCUMENTS

| | | | |
|---|---|---|---|
| 3,776,387 A | 12/1973 | Brent | |
| 3,905,311 A | 9/1975 | Carpentier | |
| 4,130,069 A | 12/1978 | Evans et al. | |
| 4,180,002 A | 12/1979 | Huempfner | |
| 4,262,809 A * | 4/1981 | McConnell | 211/192 |
| 4,351,245 A * | 9/1982 | Laporte | 108/136 |
| D266,468 S | 10/1982 | Ylanko | |
| 4,360,180 A * | 11/1982 | Bruneau | 248/162.1 |
| D274,586 S | 7/1984 | Cope et al. | |
| 4,508,305 A * | 4/1985 | Johnson et al. | 108/9 |
| 4,604,955 A | 8/1986 | Fleischer et al. | |
| D290,199 S | 6/1987 | Hampshire | |
| 4,717,112 A | 1/1988 | Pirkle | |
| 4,805,538 A * | 2/1989 | Fisher et al. | 108/7 |
| 4,927,214 A | 5/1990 | Kaufman et al. | |
| 4,938,442 A * | 7/1990 | Mastrodicasa | 248/250 |
| D339,257 S | 9/1993 | Scharer et al. | |
| D345,064 S | 3/1994 | Adams, Jr. | |
| 5,415,846 A | 5/1995 | Berry, Jr. | |
| 5,443,017 A | 8/1995 | Wacker et al. | |
| 5,511,674 A | 4/1996 | Boyd et al. | |
| 5,540,901 A | 7/1996 | Riley | |
| D372,817 S | 8/1996 | Stevens | |
| 5,598,788 A | 2/1997 | Jonker | |
| 5,598,789 A | 2/1997 | Jonker | |
| 5,660,777 A | 8/1997 | Hermann et al. | |
| 5,682,825 A * | 11/1997 | Manner | 108/147 |
| D393,382 S | 4/1998 | Rutter et al. | |
| 5,758,586 A | 6/1998 | Kieser et al. | |
| 5,845,590 A | 12/1998 | Seidl | |
| D406,201 S | 3/1999 | Olson et al. | |
| 5,938,367 A * | 8/1999 | Olson | 403/254 |
| D424,827 S | 5/2000 | Ko | |
| 6,102,497 A | 8/2000 | Ehr et al. | |
| 6,119,605 A | 9/2000 | Agee | |
| 6,189,459 B1 | 2/2001 | DeAngelis | |
| 6,253,399 B1 | 7/2001 | Wagner | |
| 6,267,111 B1 | 7/2001 | Burton | |
| 6,318,276 B1 | 11/2001 | Reinecke | |
| 6,435,112 B1 | 8/2002 | Insalaco | |
| D467,754 S | 12/2002 | Chen | |
| 6,867,393 B1 | 3/2005 | Lewis | |
| 2001/0037751 A1 | 11/2001 | Agee | |
| 2003/0024446 A1 | 2/2003 | Lanphear | |
| 2007/0024166 A1* | 2/2007 | Sung | 312/319.9 |
| 2008/0017079 A1* | 1/2008 | Looser | 108/6 |

\* cited by examiner

ADJUSTABLE BI-LEVEL SURGICAL ACCESSORY TABLE

This application is a continuation-in-part of application Ser. No. 11/948,089 filed on Nov. 11, 2007, which was a continuation-in-part of application Ser. No. 11/436,609 filed on May 19, 2006, now abandoned, which claimed benefit of provisional Application No. 60/682,851 filed on May 20, 2005.

BACKGROUND OF THE INVENTION

The invention relates generally to medical tables and, more particularly, to an improved bi-level medical table that is compact, adjustable, and easily draped.

Various types of specialized equipment are used to perform surgeries and other medical procedures. In particular, stainless-steel tables found in doctor's offices and operating rooms are used to hold a wide variety of sterilized medical instruments and supplies during surgical or other medical procedures.

Such tables arose from the need to place medical instruments and accessories within easy reach of doctors and nurses during medical or surgical procedures, and from requirements that medical instruments and supplies, as well as work surfaces of the table itself, be sterilized prior to use and kept sterile until used.

For example, many hospital regulations require routine sterilization of all parts of medical tables used in surgery that are at about thirty inches or more above the floor of an operating room. As another example, the Centers For Disease Control and various medical organizations strongly recommend the routine sterilization of medical instruments, examination tables, and other medical equipment. Because most conventional surgical tables are not easily disassembled for sterilization, the sterilization requirements are typically met by laying a sterilized disposable drape (cover) on the table surface(s) prior to the start of a medical procedure and then disposing of the drape(s) after the procedure is completed. In contrast, medical instruments and supplies are typically sterilized in an autoclave located in the hospital or other healthcare facility. Examples of acceptable instrument sterilization methods include steam under pressure, dry heat, chemical vapor, radiation, cold sterilization, or ethylene oxide gas.

Conventional surgical tables are typically made from surgical grade stainless steel and their size makes them bulky and awkward to use. Such tables generally have two or more horizontal shelves stacked one above the other and attached to four upright corner posts. The edges of the shelves and other parts of the tables are typically rounded to avoid snagging or tearing a sterilized disposable surgical drape that is laid over a particular shelf or shelves. To provide mobility, such tables are commonly equipped with an anti-static wheel at each bottom corner. The lower and upper shelves of conventional tables are structured to hold instrument sterilization trays and baskets, lap trays, scope trays, plastic baskets, wire baskets, packaged medical supplies and accessories, and other health care products.

The sizes of conventional tables vary, but a typical surgical table measures about seventy-two inches wide, about thirty-four inches high, and about twenty-four inches deep, and has a unibody construction that prevents sterilizing the table (or its components) in standard hospital autoclaves, which typically measure about three feet wide, about six feet tall, and about five feet deep. Thus, conventional surgical tables used in the operating rooms of most hospitals cannot be readily sterilized using steam under pressure, dry heat, chemical vapor, or other types of sterilization methods. Consequently, the shelves of conventional surgical tables are covered with sterile disposable surgical drapes prior to use. A typical use of a conventional surgical table is described below.

Prior to a surgery, a nurse or technician will prepare the operating room. This is typically accomplished by cleaning the surgical table using a hand-scrubbing method and/or an ultrasonic cleaning method. Once the table is cleaned, the nurse covers the table's work surface(s) with a sterilized disposable surgical drape (or drapes). After the drape(s) have been properly positioned, the nurse loads previously sterilized medical instruments and/or supplies directly onto the surgical drape(s). Generally, the instruments themselves will have been removed from the hospital autoclave a short time before; however, sterilized pre-packaged instruments and/or supplies may be loaded onto the drapes as well. Typical medical instruments and/or supplies may include kits of surgical instruments and medical devices and materials appropriate to the particular surgery that will be performed, as well as autoclave instrument sterilization trays and other sterilization receptacles. Depending on the medical procedure involved, it is not uncommon for a six foot long conventional surgical table to be covered from end to end (and front to back) with sterilized instruments and/or supplies by the time the nurse completes the preparations.

During surgery, the nurse is typically positioned between the doctor and the surgical table. From this position, the nurse can retrieve sterilized instruments and/or supplies and hand them to the doctor as necessary. The nurse can also take contaminated instruments from the doctor and place them on the surgical drape or in sterilization receptacles that were pre-positioned on the surgical table. Because most conventional surgical tables are about six feet long, the nurse often has to move back and forth from one end of the table to the other in order to retrieve (or set down) a sterilized or contaminated item. The size of the table hinders free and easy movement of the table and the people in and around the operating room. Small operating rooms further exacerbate this problem, because the bulky dimensions of a conventional surgical table leaves the nurse (and/or doctor(s)) with little floor space in which to work. Additionally, instruments and/or drapes positioned on the table may fall to the floor if the table is bumped or a drape is snagged. After the surgery or other medical procedure is finished, the drapes are considered to be biohazards, and must be properly incinerated, which increases disposal costs and adds regulatory compliance.

Health care equipment suppliers have proposed numerous approaches for configuring surgical tables and methods for sterilizing them. For instance, one conventional configuration solution adds a top shelf to the table. This top shelf is as long as the table top, but slightly narrower. Although the plane of the top shelf is not adjustable relative to the plane of the table top, the top shelf may be raised and lowered between heights of about twelve inches to about fifteen inches above the table top. This adjustability feature allows persons of about five feet four inches or less to reach instruments on the top shelf without having to use step stools. However, this conventional approach suffers drawbacks in that in addition to traversing the six foot length of the table, the nurse may also have to tilt the trays or baskets on the top shelf and/or stand on tiptoe or on a step stool) to see what instruments and/or supplies are inside. Moreover, instrument trays and other supplies are likely to fall off the narrow top shelf and cascade onto those on the table top. Additionally, use of the top shelf requires an extra disposable drape, which increases the hospital's overhead costs.

Yet another approach, disclosed in U.S. Pat. No. 4,927,214 to Kaufman et al., provides an operating room instrument table assembly formed of a plurality of modular table units. Each table unit includes castor wheel supports, a base frame attached to the castor wheel supports, a table top support frame connected to the base frame, and a removable table top detachably connected to the table top support frame. The removable table top is sterilizable as a unit with the instruments used in a medical procedure. The bare frame includes two upright posts. The table top support frame includes two tabular supports connected by a center connector. Each tabular support is sized to fit over one of the upright posts.

One disadvantage of this operating room instrument table is that it consumes a large area of floor space since only a single table top is included for each movable base/table support frame. Further, if a larger work area is desired, then separate table tops, each on its own movable base, must be disposed side-by-side, and or in a circular configuration, with the surgeon or nurse in the middle. This leads to yet another disadvantage, which is that the person handling the instruments is not free to move about the operating room, but rather is confined within the center of the modular table units. To move about the operating room, the person must push one of the modular table units out of position, and risk bumping another table unit and thereby knocking instruments into disarray and/or onto the floor. Additionally, to access instruments during a medical procedure, the person may be required to move back and forth from one portion of the table to another. During long medical procedures, this may generate fatigue and/or increase the risk that instruments may be bumped and/or dropped. In addition, only the table top is removable for sterilization. The table support frame (e.g. tubular supports connected by a center connector) remains connected to the movable base, and thus is not sterilizable with the removable table top and/or the instruments.

Another approach is disclosed in U.S. Pat. No. 6,189,459 to DeAngelis, which describes a collapsible auxiliary instrument shelf for use in surgical operating rooms. As described in this patent, a conventional surgical table includes a main shelf that is supported at each corner by a leg. A castor is attached to the bottom of each leg. The auxiliary shelf is supported above the main shelf by a pair of posts. Each post is affixed to one of the rear legs that support the main shelf.

One disadvantage of this apparatus is that neither the auxiliary shelf nor the surgical table to which it is attached are detachable for sterilization. Another disadvantage is that paper and/or clear plastic surgical drapes, with all the drawbacks referenced above, must be used to cover the auxiliary shelf and table before the auxiliary shelf and table can be used in surgery. A further disadvantage is that the auxiliary shelf cannot be angled relative to the main shelf. Consequently, it is difficult for a user of the table to view and/or access items placed on the auxiliary shelf.

Yet another proposed approach is disclosed in U.S. Pat. No. 5,551,674 to Boyd, et al., which discloses an accessory tray for use in a surgery, and, more particularly, a sterilizable accessory tray for supporting absorbent material pads for use in neurosurgery. The tray is supported on a conventional surgical stand, which has a movable base, an adjustable support pole attached the base, and a single shelf cantilevered from the top of the support pole. The accessory tray is removable from and in a fixed angular position relative to the shelf of the surgical stand. However, the shelf and other parts of the surgical stand cannot be readily disassembled and sterilized. Preferably, the accessory tray is made of a disposable plastic material, but it may also be made of a sterilizable plastic or metal material.

A disadvantage of the accessory tray of Boyd, et al. is that the tray is particularly adapted to store sterile absorbent pads commonly used in neurosurgery to absorb blood or retain accumulated blood or brain fluids, meaning it has little if any utility for other medical procedures. Although the accessory tray may be removed from the shelf and sterilized, the tray, much like a surgical drape, is preferably removed and thrown away. Consequently, each use of the surgical stand requires either a new sterilized disposable drape or a new sterilized accessory tray. Another disadvantage of this apparatus is that the shelf of the surgical stand is equipped with a continuous raised lip that tends to retain blood and other fluids drained from any used surgical instruments and/or supplies that may be placed on the shelf during a procedure.

Recent medical studies have generated stringent sterilization requirements, most of which are difficult or impossible to satisfy simply by hand cleaning and ultrasonic cleaning alone. In addition to being bulky and non-ergonomic, conventional surgical tables are difficult to sterilize and are costly because they require the use of expensive sterilized disposable drapes.

Thus, there is a need for an improved configuration of a surgical table, particularly a compact table, used during surgery in a hospital operating room, which is easier to sterilize and use in surgery than conventional surgical tables.

SUMMARY OF THE INVENTION

The invention meets the foregoing needs and avoids the drawbacks and disadvantages of the prior art by providing a compact, ergonomically-designed, medical table for use in surgery and other medical procedures that has components that may be readily disassembled and sterilized in a standard autoclave of the type typically found in hospitals.

A table manufactured according to the invention may be used in surgeries or other medical procedures performed in human health care facilities or in animal health care facilities. Both types of medical facilities may include autoclaves or similar sterilizers. The table of the invention may be used either to store medical equipment and/or instruments or as a workspace for performing a medical procedure. Users of a table manufactured according to the invention may include, but are not limited to, veterinarians, traditional doctors and surgeons, medical staff, and other persons who work in the animal or the health care industry.

Accordingly, in one aspect of the invention, a modular surgical table has a movable base which supports two removable tabletops. A first sterilizable tabletop structured to hold sterilized medical instruments and supplies during a medical procedure is supported by a pair of uprights at the front of the base. A second sterilizable tabletop is supported by another pair of uprights at the rear of the base. Each of the tabletops is removable so that it can be sterilized separately.

The forward tabletop has an upper surface which is at a level completely below the rearward tabletop. The second tabletop is vertically higher the first tabletop, and is situated behind the first tabletop. The second tabletop can be tilted to various angles when a release pedal is depressed, but is normally locked at a set angle. The forward tabletop cannot tilt, but it can be moved fore and aft when another pedal is depressed. Normally, the forward tabletop's position is locked as well.

The inventive table can store about the same quantity of surgical instruments and packaged medical supplies as a conventional surgical table, but within a smaller floor area, for example, about forty inches by about thirty-eight inches. This configuration saves floor space and allows a nurse or other user to readily retrieve instruments and supplies while standing or sitting in a virtually stationary position.

Additional features, advantages, and embodiments of the invention may be set forth in the following detailed description.

DETAILED DESCRIPTION OF PREFERRED EMBODIMENTS OF THE INVENTION

Figure 1:
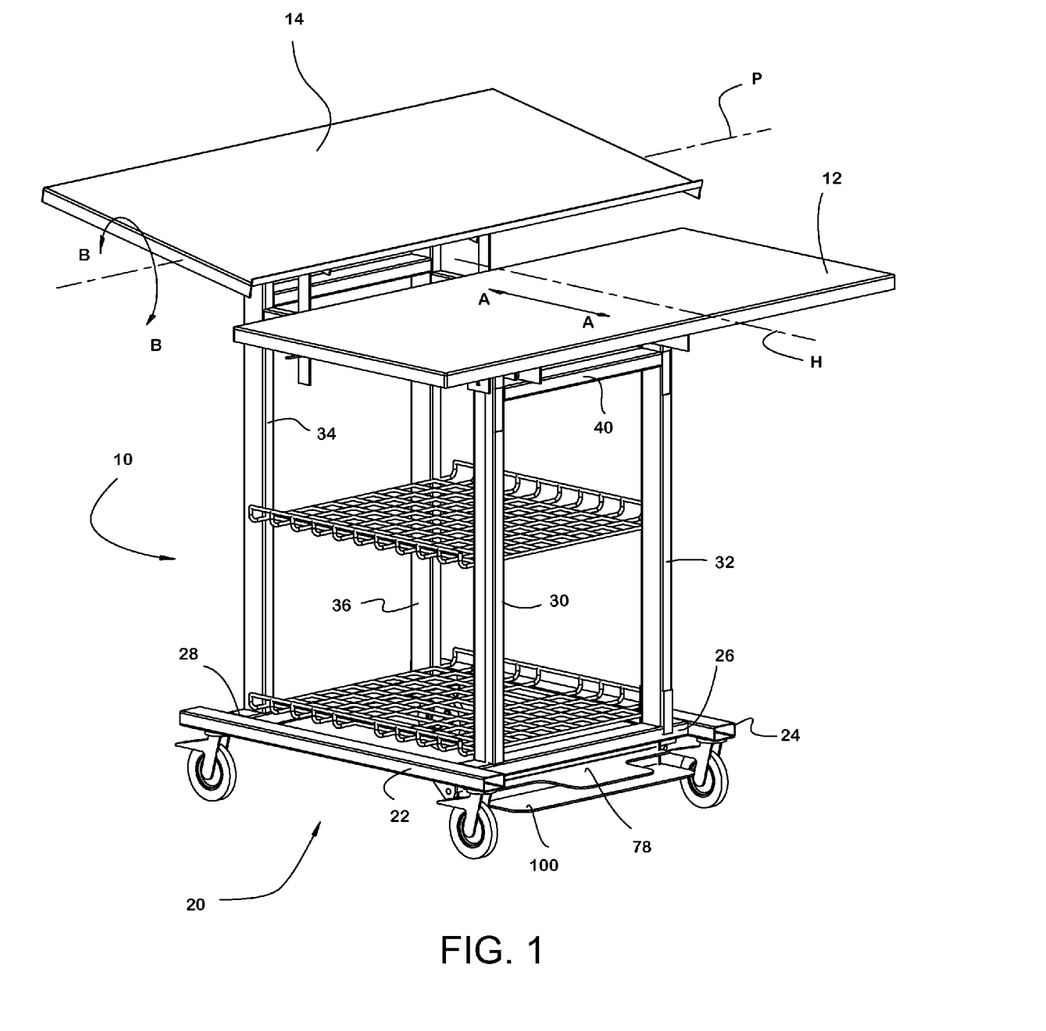
FIG. 1 is a perspective view from the front and one side, of a surgical accessory table embodying the invention.

As shown in FIG. 1, a surgical accessory table embodying the invention includes a base 10, which supports two independent tabletops 12, 14.

The Base

The base includes a rectangular bottom frame 20, which preferably has wheels or casters at four corners. Preferably, at least some of the wheels have a locking mechanism (not shown) to immobilize the table when desired. The frame 20 illustrated is formed from four rectangular section box channel elements 22, 24, 26, 28, but other designs are possible.

Four uprights 30, 32, 34, 36 are welded to the frame, near its corners. The uprights shown are hollow box channel members, but other shapes may be suitable. The rear uprights 34, 36 are taller than the front uprights 30, 32 so as to maintain the rear tabletop at a greater height than the front tabletop.

"Front" should be understood to mean the side of the device having the shorter uprights. "Rear" means the side having the longer uprights. "Fore and aft" means from front to rear and vice-versa. "Lateral" means left to right and vice-versa. "Horizontal" herein means geographically horizontal, when the device is standing upright on a level floor.

Figure 3:
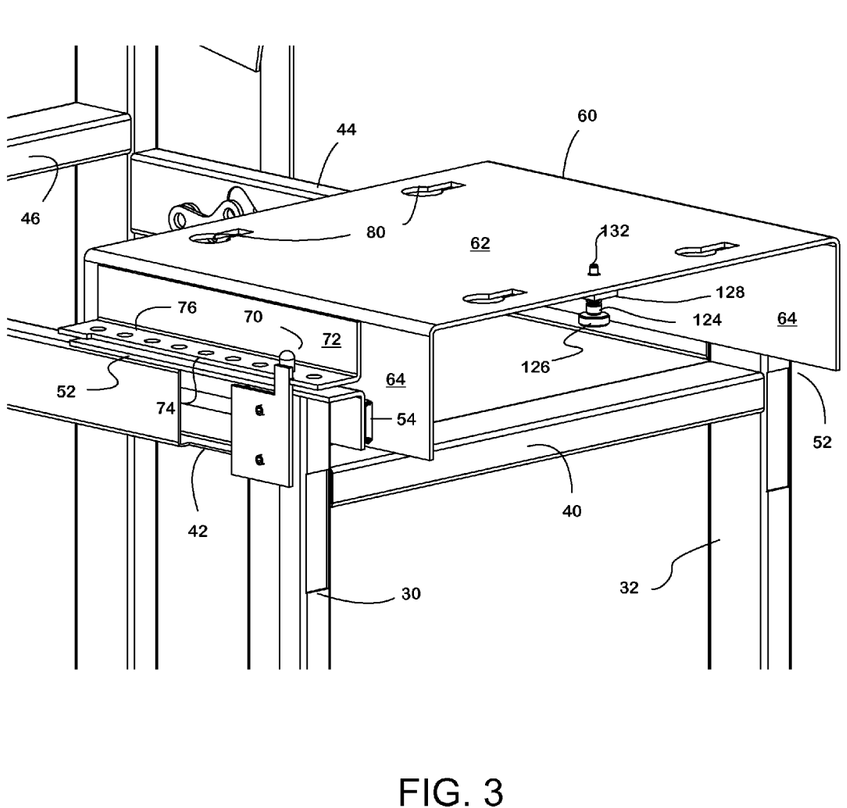
FIG. 3 is an enlarged perspective view thereof, showing structure which supports the forward tabletop.
Figure 4:
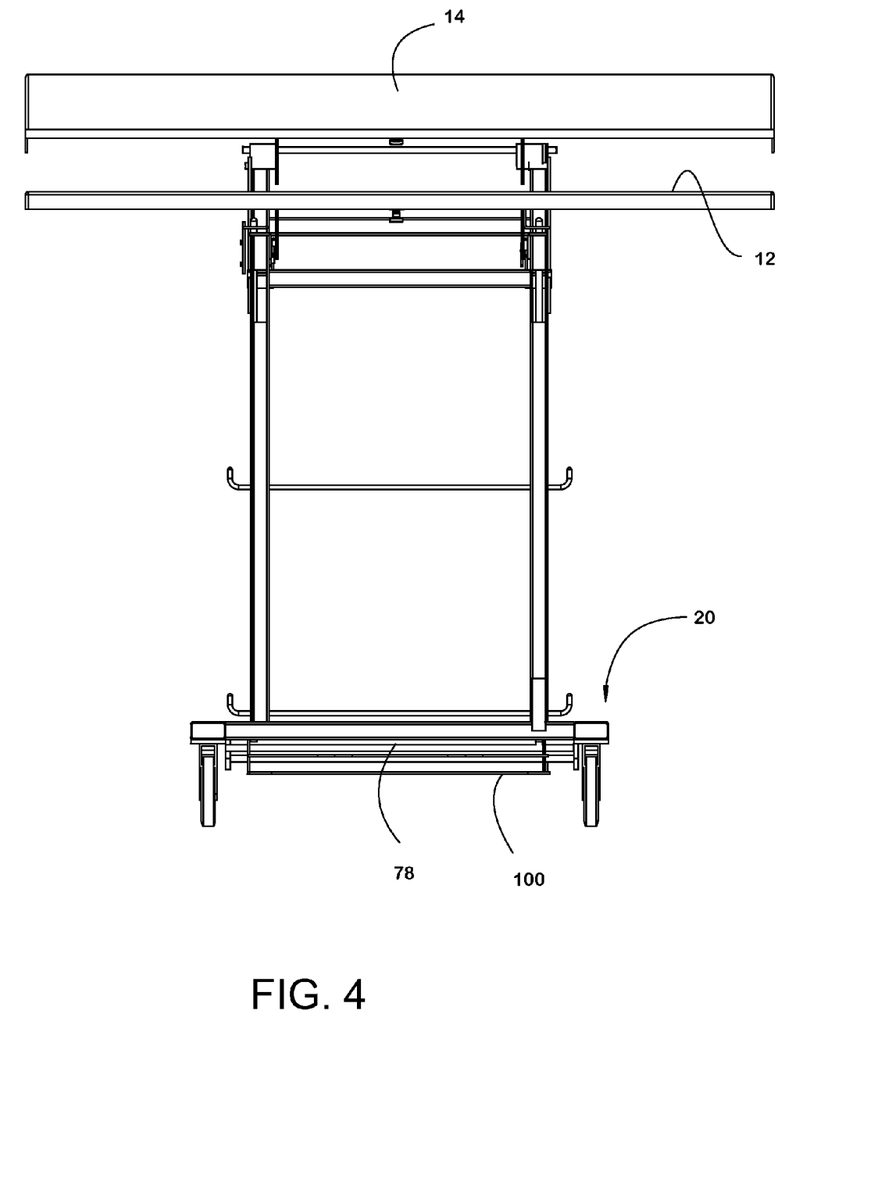
FIG. 4 is a front elevation of the table shown in FIG. 1.

Horizontal braces 40, 42, 44, 46 (FIG. 3) interconnect the upper ends of the four uprights to rigidify the base. Two stationary, parallel brackets 52 (only one of which is visible in FIG. 3) are connected to the braces 42, 44, preferably by welding. These brackets extend forward slightly past the uprights 30, 32.

The Carriage

Figure 2:
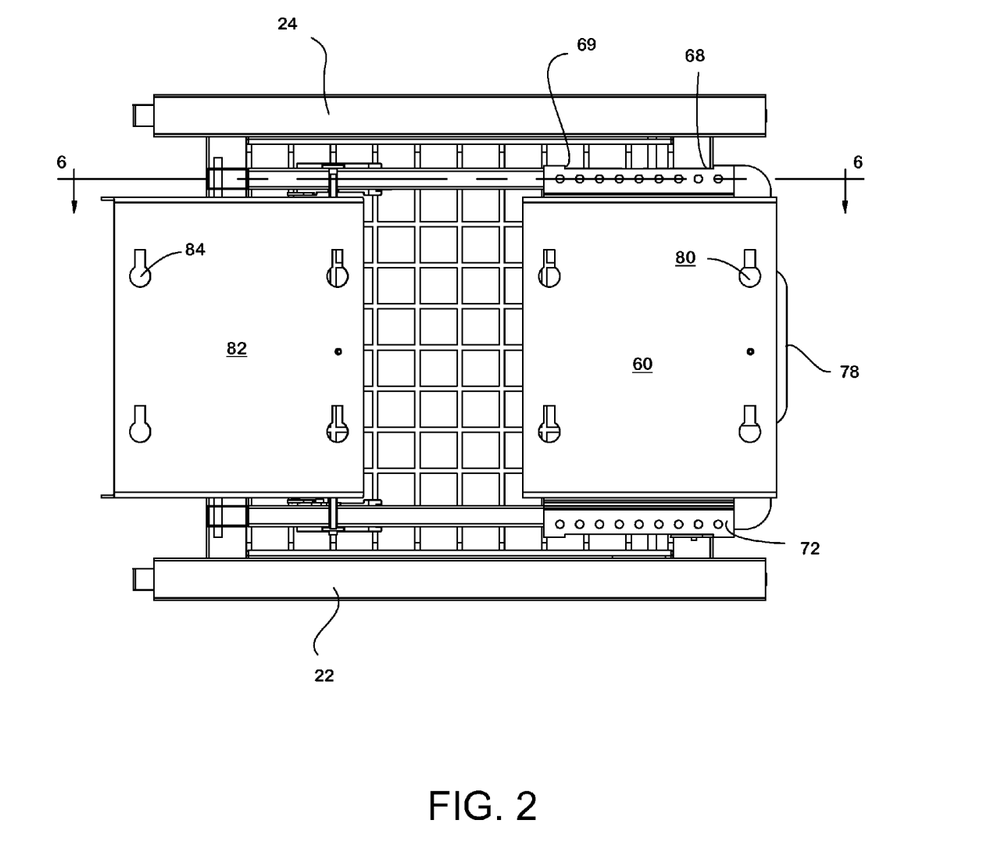
FIG. 2 is a top plan view thereof, with the table's tops removed.

As seen in FIG. 2, the front tabletop (which has been removed in this view) is supported by a carriage 50 which permits the front tabletop to move fore and aft in a horizontal plane, as suggested by the arrows "A" in FIG. 1, but prevent it from moving vertically. The carriage is described in detail below.

Each of the stationary carriage brackets 52 has a telescoping slide 54 affixed to it. Preferably, each of the slides is made of heavy-duty stainless steel and comprises two relatively slidable parts: a stationary part 56 secured to the carriage bracket, and a movable part 58 connected to the body 60 of the carriage. Ball bearings (not shown) are contained between the two parts, to eliminate sliding friction.

The carriage body 60 is substantially rigid, being made from heavy gauge metal sheet. It has a flat central portion 62 with downturned flanges 64 at opposite lateral edges. The movable slide parts 58 are connected to these flanges by screws or rivets.

The slides 54 support the carriage body 60 and enable it to move unidirectionally along the fore-and-aft horizontal axis "H", which is parallel to the slides. The carriage body cannot move in any other direction, and cannot yaw, pitch or roll. Its motion fore and aft is limited by a stop plate 66 (FIG. 5) affixed to the base. The finger 68 protruding upward from the stop plate engages shoulders 69 (FIG. 2) at either end of the carriage, to define the extremes of travel.

The carriage is normally prevented from moving along its fore-and-aft axis "H" by a pair of latch pins 70 (FIG. 3) which extend upward through the respective front uprights of the base to and through the carriage brackets 52. A steel angle element 72 is securely fixed to each of the flanges of the carriage, with the protruding horizontal flange 74 of each angle element in the path of one of the latch pins. This flange has a series of holes 76, into any one of which the pin can enter from below to immobilize the carriage. A spring (not shown) within the upright biases each pin 70 upward, causing the pin to seat in one of the holes.

A pedal 78 (the narrower upper pedal, FIG. 1) is attached to the lower ends of the pins, near the bottom of the base, to disengage the pins from the holes. Pressing on the upper pedal retracts the pins 70 from the holes 76 in the horizontal flanges 74, freeing the carriage so that the position of the forward tabletop 12 can be adjusted.

Figure 5:
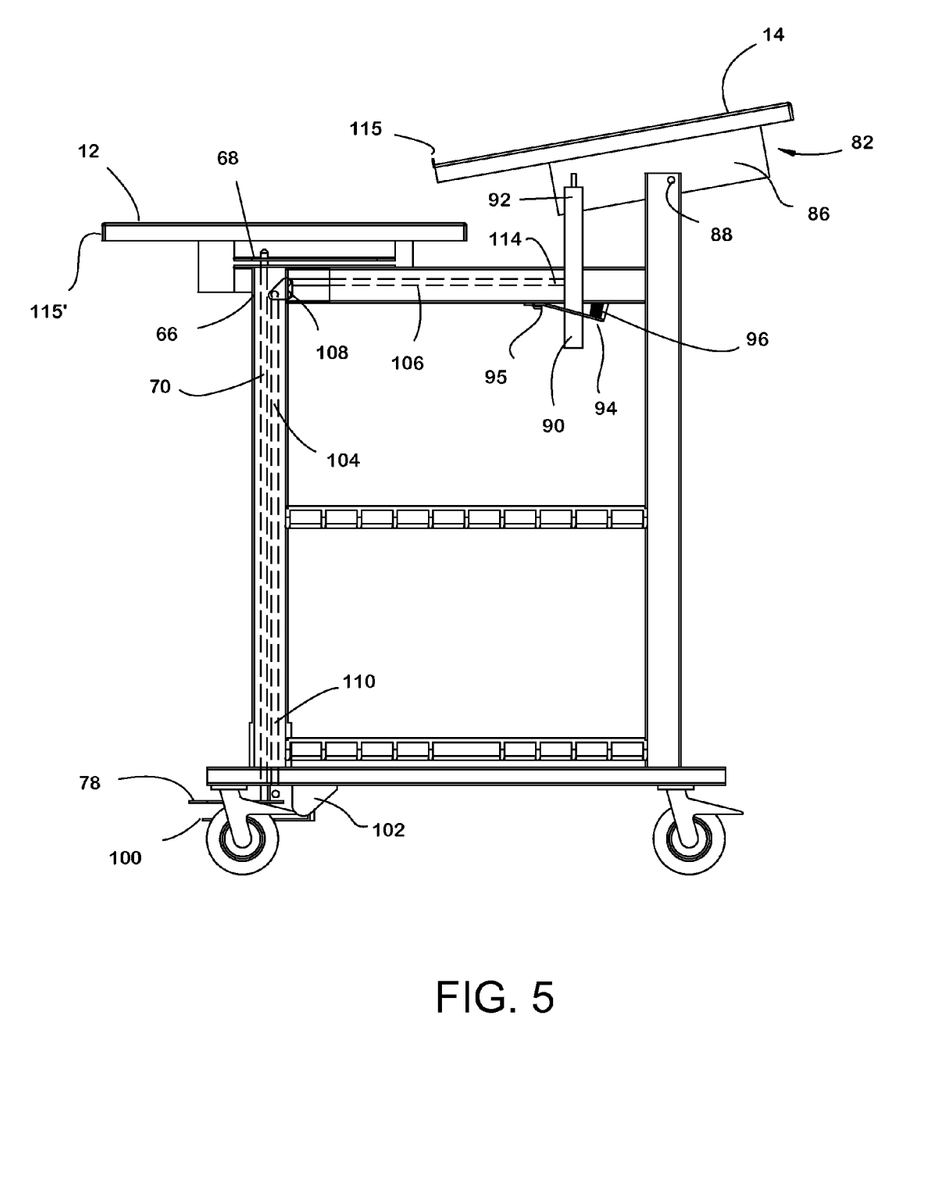
FIG. 5 is a sectional view, taken on the plane 6-6 in FIG. 2, showing a linkage for releasing the tilt adjusting mechanism and a linkage for releasing the carriage.

When the front tabletop is set in its most rearward position, its rear edge lies beneath the upper tabletop. When the front tabletop is pulled fully forward, there is a gap of about four inches (horizontally) between the tabletops, as shown in FIG. 5.

Referring again to FIG. 3, keyhole-shaped apertures 80 (preferably four) are formed in the central portion 62 of the carriage body. The apertures are aligned all facing the same way, with their larger ends to the left, and their lengths running in a lateral direction. The function of the apertures is described further below.

The Tilt Adjusting Mechanism

The rear tabletop 14, like the front tabletop 12, is supported by a substantially rigid body 82, which has a central portion in which keyhole-shaped apertures 84 (FIG. 2) are formed. The body 82 has downturned lateral flanges 86 which have pivot connections to the rear uprights. This enables the rear tabletop to be tilted fore and aft; however, it cannot be moved linearly in any direction.

The preferred pivot connection is a transverse rod 88, which forms a pivot axis "P" (see FIG. 1) about which the rear tabletop can be manually tilted forward (toward the front tabletop) from about 0° to about 10° with respect to horizontal. The transverse rod is welded to the rear uprights and passes through holes in the flanges 86.

Figure 6:
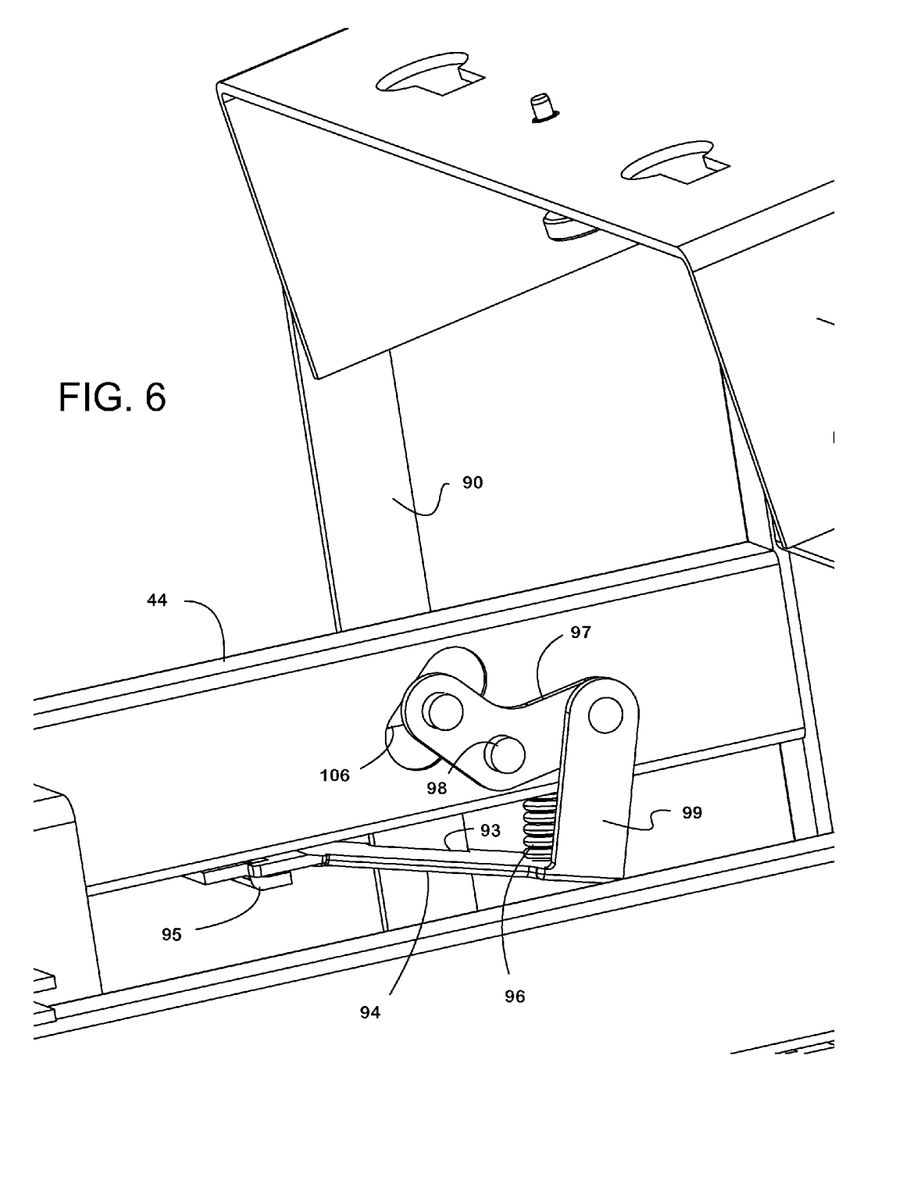
FIG. 6 is an enlarged perspective view of a portion of the mechanism shown in FIG. 5.

The rear tabletop is normally locked in position, so that its tilt angle cannot change, by two elongate prop members 90, one on either side of the unit. Each prop member 90 is pinned at its upper end 92 to the flange 86 of the body 82. As seen in FIG. 6, the lower end of the prop member passes through a slot 93—slightly wider than the width of the prop member—formed in a locking plate 94 which is hinged by means of a retaining member 95 to the bottom of one of the braces 42, 44. A coil compression spring 96 biases the locking plate downward, away from the brace, toward a binding position which clamps the prop member and prevents the tabletop angle from changing.

Each locking plate is operatively connected to the broad, lower pedal 100, which is pivotally supported by brackets 102 attached to either side of the base. The preferred operative connection is a linkage including a vertical rod 104, which extends upward from the first pedal within the vertical member, and a horizontal rod 106 which extends within the horizontal member. A first rocker arm 108 is pivotally attached to the base at the intersection of the horizontal and vertical members, and the rods are pinned to different points of the rocker arm, which converts vertical motion on the vertical rod to horizontal motion of the horizontal rod. The lower end 110 of the vertical rod is pinned to a plate 112 on the first pedal, and the far end 114 of the horizontal rod is pinned to the locking plate 96.

The rear end of the horizontal rod 106 is pinned to a second rocker arm 97, which oscillates about a pin 98 attached to the frame member 44. The rocker arm in turn is pinned to the locking plate's extension 99.

Depressing the lower pedal 100 causes the linkage to retract the locking member to a non-binding position, whereupon the rear table's tilt angle can be adjusted. Releasing the pedal 100 allows the spring to return the locking plate 96 to its binding position, which clamps to prop member 90 to lock the rear table at its set tilt angle.

The Tabletops

The tabletops are identical, with one exception: the rear tabletop 14 has an upturned lip 115 (FIG. 5) along its lowermost edge, to prevent small items from rolling off when the tabletop is tilted forward. The corresponding edge 115' on the front tabletop 12 is turned downward.

Figure 7:
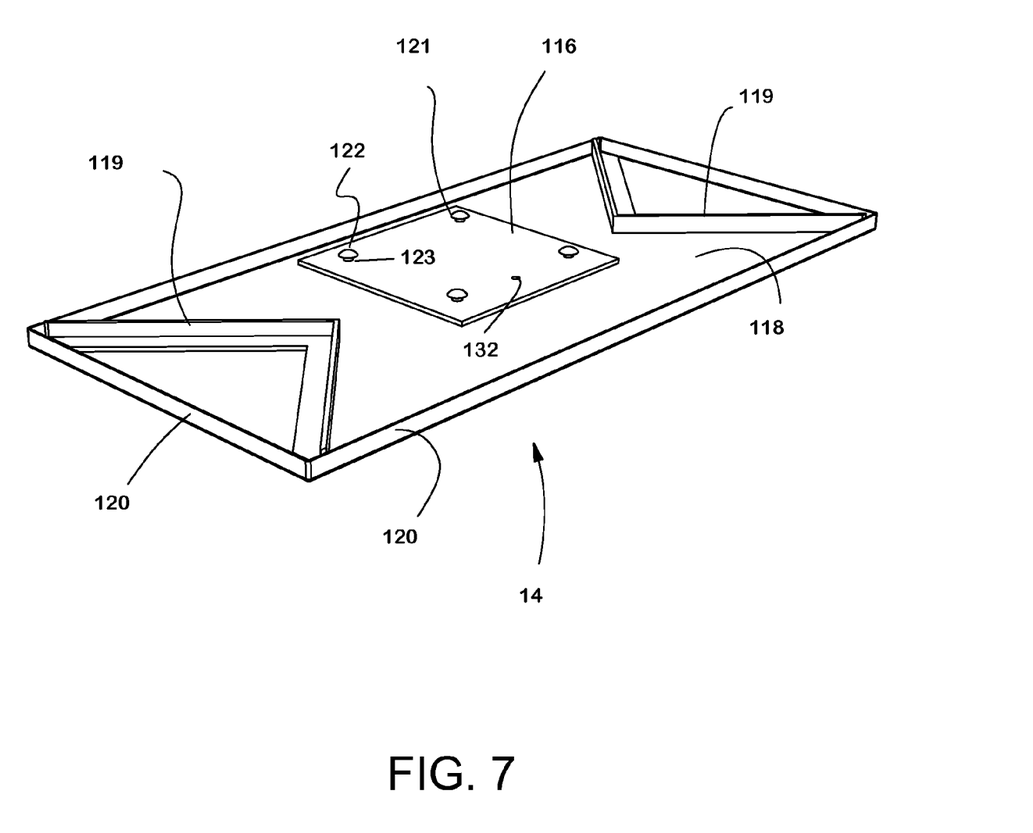
FIG. 7 shows one of the tabletops in an inverted position.

One of the tabletops is shown upside down in FIG. 7, to reveal a base plate 116 and a sheet metal panel 118 spot welded to the base plate. The panel has peripheral flanges 120 which reinforce the tabletop against bending. The base plate 116 reinforces the center of the panel, and pairs of reinforcing channel members 119, arranged in two vees, are spot welded to the panel to reinforce its outer portions against bending.

Four headed studs 121 are welded to the base plate, in a pattern corresponding to that of the keyhole apertures in the carriage. The heads 122 of the studs are sized to fit through large ends of the keyholes, and their necks 123 are sized to fit within the small ends of the keyholes, so the front table can be installed on the carriages simply by inserting the studs heads into the keyholes, and then moving the top laterally—in a horizontal direction perpendicular to the movement axes of the carriage—to lock the top to the carriage. A person cannot accidentally disengage the tabletop by leaning against the front end of the table, or by pushing or pulling on it (while stepping on the appropriate pedal to reposition the table): a deliberate lateral force is required.

To provide added security against accidental dislodgement of the tabletops, a retractable plunger 124 (FIG. 3) is mounted on the bottom of the carriage. Suitable plungers are available from Vlier, Inc., Hopkinton, Mass. (model No. SSLF375 or SSLF250). This plunger comprises a spring-loaded element which is normally extended but can be retracted by turning the knurled knob 126 in either direction a part-turn. The device has a threaded body and is installed in a nut 128 which is retained on the bottom surface of the carriage, midway between the two outboard keyhole slots. The plunger tip 130 is slightly tapered, and seats in a hole 132 drilled in the base plate. When the tabletop is installed on the carriage, and the studs are seated in the narrow ends of the keyhole slots, the tip snaps into the hole in the plate, and prevents the tabletop from being removed until the tip is deliberately withdrawn from the hole by the user.

The invention is subject to modifications and improvements. For example, one or more of the raised lips of the rear shelf and/or one or more of the raised lips of the front shelf may be replaced with a contoured shelf rod (not shown), which is raised approximately one-half inch from the shelf's planar surface so liquids can drain. Also, the tabletops may be labeled by being laser cut or embossed, e.g.: FR for front right, FL for front left, RR for rear right, and RL for rear left, to aid in assembly or reassembly of the table.

Another possible modification is that each of the uprights 30, 32, 34, 36 could be made in two telescoping pieces so that the height of the base, and thus the level of both tabletops, could be adjusted.

The examples given above are merely illustrative and are not meant to be an exhaustive list of all possible designs, embodiments, applications or modifications of the invention defined below.

We claim as our invention:

1. A surgical accessory table comprising
a structural base,
a carriage supported by said base, said carriage comprising a planar segment and a pair of flanges formed at opposite ends of the planar segment, the planar segment having plural keyhole apertures formed therein,
the carriage being attached to the base by slides which permit the carriage to move linearly along a fixed, horizontal axis, and prevent the carriage from moving vertically or laterally, or yawing, pitching or rolling with respect to the base,
a first tabletop having a top surface lying in a horizontal plane, said tabletop being connected to said carriage, and
a second tabletop having a top surface lying in a plane which is non-coextensive with said horizontal plane, the second tabletop being supported by the base and lying entirely above said horizontal plane of the first tabletop,
a first mechanism for releasably holding said first tabletop in a set position,
a second mechanism for releasably holding said second tabletop in a set position,
said first mechanism comprising a first release pedal near the bottom of said base, and
said second mechanism comprising a second release pedal near the bottom of the base,
whereby an operator may release and adjust the position of either tabletop, and wherein
the structural base is formed from hollow channel members, and both pedals are connected to their respective mechanisms by rods which run inside said channels.

2. The invention of claim 1, wherein said second tabletop can be tilted about a horizontal axis, but cannot be moved linearly in any direction.

3. The invention of claim 2, wherein said horizontal axis extends transverse to and above the movement axis of the carriage.

4. The invention of claim 2, wherein said second mechanism comprises a prop member pinned at its upper end to the second tabletop, and extending through a locking mechanism, said locking mechanism clamping said prop member when in an active position to prevent the second tabletop from tilting, and permitting tilting when in a release position.

5. The invention of claim 4, further comprising a spring for biasing the locking mechanism toward its active position.

6. The invention of claim 4, wherein the first holding mechanism comprises a rear table releasing pedal supported by the base, and linkage connecting said pedal to the locking mechanism, whereby the locking mechanism may be moved to its release position by depressing the pedal so that the table may be tilted.

7. The invention of claim 6, wherein the linkage comprises a vertical rod connected to the rear table releasing pedal, a rocker arm pivotally connected to the base, and a horizontal rod connected to the locking mechanism, both said rods being connected to the rocker arm.

8. The invention of claim 1, further comprising at least one stop to limit movement of the carriage to prevent the tops from striking one another.

9. The invention of claim 1, wherein the second holding mechanism comprises a latch mechanism for maintaining the carriage in a fixed position.

10. The invention of claim 9, wherein the latch mechanism comprises at least one element, affixed to the carriage, having plural holes therein and at least one movable pin, contained within the base, capable of entering any one of the holes.

11. The invention of claim 10, further comprising a spring for biasing the pin into engagement with one of said holes.

12. The invention of claim 10, wherein the second holding mechanism comprises a front table releasing pedal connected to at least one of the pins in such a way that depressing said pedal retracts the pin connected thereto out of engagement with said holes.

13. The invention of claim 1, wherein each of the tabletops is releasably connected to a respective one of said carriages by a respective array of stud fasteners.

14. The invention of claim 13, wherein each array of stud fasteners extend from one of the tabletop and the carriage, and further comprising a corresponding array of plural keyhole apertures formed in the other of the carriage and the tabletop.

15. The invention of claim 14, wherein the keyhole apertures in each array are aligned all in the same direction, with their length perpendicular to the axis of movement of the respective carriage.

16. The invention of claim 15, wherein the keyhole apertures on one array are aligned in a direction opposite those of the keyhole apertures on the other array.

17. The invention of claim 1, further comprising a locking device comprising a retractable plunger which seats in a hole in the tabletop to prevent the stud fasteners from being disengaged accidentally from the keyhole slots.

* * * * *